United States Patent [19]
Rowlands et al.

[11] Patent Number: 5,919,906
[45] Date of Patent: Jul. 6, 1999

[54] PROTEASE PRODUCED GELATIN

[75] Inventors: Anne G. Rowlands, Honeoye Falls; Deborah J. Burrows, Rochester, both of N.Y.

[73] Assignee: Eastman Kodak Company, Rochester, N.Y.

[21] Appl. No.: 09/186,433

[22] Filed: Nov. 5, 1998

[51] Int. Cl.⁶ .......................... C08L 89/00; C09D 189/00
[52] U.S. Cl. ........................................ 530/354; 106/160.1
[58] Field of Search .......................... 530/354; 106/160.1

[56] References Cited

U.S. PATENT DOCUMENTS

| | | |
|---|---|---|
| 2,761,791 | 9/1956 | Russell . |
| 3,508,847 | 4/1970 | Martin . |
| 3,539,644 | 11/1970 | Burness et al. . |
| 4,655,840 | 4/1987 | Wittwer et al. ........................ 106/126 |
| 5,034,249 | 7/1991 | Reif et al. . |

FOREIGN PATENT DOCUMENTS

| 257515 | 3/1988 | European Pat. Off. . |
|---|---|---|

OTHER PUBLICATIONS

Research Disclosure, Dec. 1989, no month avail. No. 308119.

*Primary Examiner*—David Brunsman
*Attorney, Agent, or Firm*—Carl F. Ruoff

[57] ABSTRACT

The present invention describes a gelatin having a high molecular weight fraction (>250,000 Daltons) of from 0 to 25 wt %, a beta fraction (150,000–250,000 Daltons) of from 0 to 20 wt % and an alpha fraction (50,000–150,000 Daltons) of from 15 to 55 wt %. The gelatin has a gel strength of from 200 to 400, an absorbance a 420 nm of from 0 to 0.068 and a concentration of protease of greater than 10 ppb.

2 Claims, No Drawings

PROTEASE PRODUCED GELATIN

CROSS REFERENCE TO RELATED APPLICATIONS

This application relates to commonly assigned copending application Ser. No. 09/185,440, filed simultaneously herewith. This application relates to commonly assigned copending application Ser. No. 09/185,441, filed simultaneously herewith. This application relates to commonly assigned copending application Ser. No. 09/185,209, filed simultaneously herewith.

FIELD OF THE INVENTION

The present invention relates to the production of gelatin. More, particularly the present invention describes a high quality gelatin for use in imaging applications.

BACKGROUND OF THE INVENTION

In the manufacture of photographic films and papers, a support is commonly coated with multiple layers. The different layers have different individual functions in the final product, and in many instances it is necessary that the layers remain distinct and not mix with one another. For example, a simple color photographic film can have a subcoating, a blue-sensitive layer, a green-sensitive layer, a red-sensitive layer, one or more color filtering coatings, etc. Films with about 15 layers have been described, e.g. in EP 257,515, incorporated by reference herein.

In forming photographic elements, the layers can be applied to the support by various procedures known in the art. For example, the layers can be applied by dip coating, roller coating, spray coating, bead coating, and the like.

Two or more layers can be simultaneously applied as illustrated by U.S. Pat. Nos. 2,761,791, 3,508,847, 3,539,644, and such other patents cited in Research Disclosure No. 308, December 1989, pp. 1007–8, incorporated by reference herein. There, coating and drying procedures are discussed.

High purity gelatins are required for (imaging/photographic) applications. One gelatin property of interest is absorbance at 420 nm (A420), commonly know as color. The lower the A420 of gelatin the clearer the gelatin layer is in coated products. The A420 of gelatin is one of the defining factors for determining applicability of the gelatin for imaging applications. Edible gelatins are typically higher than photographic gelatins in A420. Two other gelatin properties critical to imaging applications are viscosity and Gel or Bloom strength. High Gel strength is required for gelatin setting properties. Typical alkaline processed bone gelatins contain high Gel strength and high viscosity. Viscosity is typically controlled during the gelatin manufacturing process with heat treatment. Heat treatment reduces both Gel strength and viscosity. Ideally, a gelatin with high Gel strength and low viscosity would be advantageous to coated products, in that coating speeds could be increased with no loss in gelatin setting properties. The gelatin described in this invention is optimized for each of the properties described above. This novel gelatin combines very low color and high Gel strength within a wide range of viscosities. Typically, photographic gelatin requires a Gel strength of greater than 200 and a viscosity of from 7 to 9 cp.

SUMMARY OF THE INVENTION

The present invention describes a gelatin having a high molecular weight fraction (>250,000) of from 0 to 25 wt %, a beta fraction (150,000–250,000) of from 0 to 20 wt % and an alpha fraction (50,000–150,000) of from 15 to 55 wt %. The gelatin has a gel strength of from 200 to 400, an absorbance at 420 nm of less than 0.068 and a concentration of protease of greater than 10 ppb.

DETAILED DESCRIPTION OF THE INVENTION

The present invention describes a gelatin manufactured from collagen containing material utilizing proteolytic enzymes to extract gelatin. A collagen containing material demineralized to produce ossein is homogenized or ground and added to a solution of protease for sufficient time to extract gelatin at a predetermined viscosity. Following extraction the gelatin may be clarified, filtered, oxidized or deionized to achieve desired levels of microconstituents, prior to concentration and drying. The rate of enzyme action on ossein is a function of enzyme concentration, pH, temperature and time. Optimization of these factors is enzyme dependent.

Typical collagen containing materials include skins, bones, hides and connective tissue of an animal body. Sources of animal bodies include cows, pigs and sheep. The most preferred source for collagen for production of high quality gelatin is cow bone.

Due to variable bond breakage during manufacture, gelatin is composed of a distribution of proteins of varying lengths. Aqueous size exclusion chromotagraphy provides a method of analysis for determining the gelatin molecular weight distribution. This distribution is described as containing the following fractions; high molecular weight or HMW (>250 Kdaltons); Beta (250–150 Kdaltons); Alpha (150–50 Kdaltons); Subalpha (50–20 Kdaltons); and low molecular weight or LMW (20–4 Kdaltons). In general, high gel strength correlates with high gelatin alpha fraction content, and high viscosity correlates with high gelatin HMW fraction content.

Enzymes are biological catalysts. Similar to traditional chemical catalysts, enzymes speed the rate of biological reactions by producing a transition state with a lower energy of activation than the uncatalyzed reaction. Unlike traditional chemical catalysts, enzymes are biological in nature. Enzymes are proteins specialized for the reactions they catalyze. In other words enzymes exhibit substrate specificity. Proteases are enzymes that catalyze the hydrolysis of peptide bonds in proteins and peptides.

Enzymes are irreverisbly inactivated by agents or processes which covalently and permanently modify the active site of the enzyme. Typically, reactions which denature proteins achieve this affect. For example extremes in pH or elevated temperatures.

Purification of enzyme extracted gelatin can be varied to achieve the desired level of microconstitutents. Filteration can be combined with deionization, oxidation, or a clarification process. The clarification process described in U.S. Ser. No. 09/185,441 removes non-gelatin proteins and lipids through flocculation. Following purification, sequential enzyme produced gelatin extractions may be blended in liquid form prior to concentration. Concentration is achieved through an evaporative process. Concentrated gelatin can be used in liquid, chilled or dried form.

The present invention is described with particular reference to the following Examples.

The present invention describes a gelatin very low in color (A420 nm) combined with high Gel Strength over a wide range of viscosities. Enzyme manufactured gelatin as described in U.S. Ser. No. 09/185,440 was compared to a gelatin typical of a traditional alkaline liming process.

|  | Limed ossein gelatins | | | Enzyme extracted gelatins |
|---|---|---|---|---|
|  | LOG 1 | LOG 2 | LOG 3 | EG 1 |
| Molecular Weight Fractions | | | | |
| HMW | 20.44 | 28.76 | 25.79 | 4.22 |
| BETA | 17.19 | 17.37 | 17.41 | 8.56 |
| ALPHA | 51.13 | 40.79 | 45.13 | 38.09 |
| A420 | 0.057 | 0.12 | 0.08 | 0.067 |
| Viscosity (cps) | 7.62 | 8.95 | 8.5 | 4.1 |
| Gel Strength (g) | 295 | 260 | 275 | 250 |

LOG 1 A blend of early extractions of lime processed ossein gelatin
LOG 2 A blend of late extraction of lime processed ossein gelatin
LOG 3 A blend of early and late extractions of lime processed ossein gelatin
EG 1 Protease extracted gelatin from fully limed ossein (all extractions combined)

The present invention provides a gelatin of extremely low color (less than 0.068 absorbance at 420 nm) and the ability to control viscosity of the gelatin without loss of gel strength. It is preferred that the protease concentration of the gelatin be at least 10 ppb, most preferably at least 1 to 10 ppm. The addition of increasing amounts of protease increases the reaction but after a certain amount of protease the reaction proceeds to quickly to control and the resulting gelatin loses integrity. Moreover the gelatin of the present invention has a lower viscosity (approximately 4 cp) which is advantageous in coating. However gelatin of the present invention can have a viscosity of from 2 to 10 cp.

Molecular weight distribution of gelatin was determined by high-performance liquid chromatography in the aqueous size exclusion mode. Gelatin samples were dissolved in the chromatographic eluent, a phosphate buffer containing sodium dodecyl sulfate. Different molecular weight fractions were separated on a Toso Haas TSK Gel size exclusion column and the effluent monitored with a UV detector set at 220 nm. Known molecular weight standards were used to prepare a calibration curve, which was constructed by plotting the log of molecular weight versus retention time. The molecular weight distribution of the gelatin samples was determined from the linear portion of this calibration curve.

Absorbance at 420 nm was measured using a 6.16% gel solution moisture corrected. Viscosity of 6.16% moisture corrected gelatin solutions were determined using a Brookfield viscometer. Gel strength was determined by analysis of a chilled 6.16% gel solution with a Voland-Stevens Texture Analyzer.

The process and materials of this invention can be used for any imaging material using gelatin. For example, they can be used for color photographic materials such as color photographic negative films, color photographic reversal films, color photographic positive films, color photographic papers, color photographic reversal papers, and color photographic materials for a color diffusion transfer system and a silver dye bleach system, and for black-and-white photographic materials such as black-and-white photographic films, radiographic films, graphic films, black-and-white photographic papers, navigational photographic films, microfilms, facsimile films, photocomposing films or papers, graph films, etc. Ink jet applications are also contemplated.

Also, gelatin to which this invention is applied may be, if necessary, partially replaced with colloidal albumin, casein, cellulose derivatives (e.g., carboxymethyl cellulose, hydroxyethyl cellulose, etc.), sugar derivatives (e.g., agar agar, sodium alginate, starch derivatives, etc.), and synthetic hydrophilic colloids (e.g., polyvinyl alcohol, poly-N-vinyl pyrrolidone, polyacrylic acid copolymers, polyacrylamide, and derivatives or partially hydrolyzed products thereof) as well as gelatin derivatives modified by the treatment of an amino group, an imino group, a hydroxy group, or a carboxy group contained in the gelatin molecule as a functional group with a reagent having one group capable of reacting the group, or a gelatin graft polymer prepared by bonding gelatin to the molecular chain of another polymeric material.

The invention has been described in detail with particular reference to certain preferred embodiments thereof, but it will be understood that variations and modifications can be effected within the spirit and scope of the invention.

What is claimed is:

1. Gelatin comprising:

a high molecular weight fraction (>250,000 Daltons) of from 0 to 25 wt %;

a beta fraction (150,000–250,000 Daltons) of from 0 to 20 wt %;

an alpha fraction (50,000–150,000 Daltons) of from 15 to 55 wt %;

wherein said gelatin has a gel strength of from 200 to 400, an absorbance at 420 nm of less than 0.068 and a concentration of protease of greater than 10 ppb.

2. The gelatin of claim 1 further comprising a viscosity of from 2 to 10 cP.

* * * * *